United States Patent [19]

Heitmann

[11] Patent Number: 4,974,443
[45] Date of Patent: Dec. 4, 1990

[54] METHOD OF AND APPARATUS FOR ASCERTAINING THE HARDNESS OF CIGARETTES AND THE LIKE

[75] Inventor: Uwe Heitmann, Hamburg, Fed. Rep. of Germany

[73] Assignee: Körber AG, Hamburg, Fed. Rep. of Germany

[21] Appl. No.: 428,459

[22] Filed: Oct. 30, 1989

Related U.S. Application Data

[63] Continuation of Ser. No. 261,840, Oct. 24, 1988, abandoned.

[30] Foreign Application Priority Data

Oct. 28, 1987 [DE] Fed. Rep. of Germany ....... 3736447

[51] Int. Cl.$^5$ .............................................. G01N 3/48
[52] U.S. Cl. ........................................ 73/81; 131/906
[58] Field of Search ................ 73/78, 79, 81, 82, 788, 73/794, 795, 818, 849; 131/906–910, 84.1–84.4

[56] References Cited

U.S. PATENT DOCUMENTS

| | | | |
|---|---|---|---|
| 2,667,172 | 1/1954 | Broekhuysen et al. | 131/906 |
| 3,742,795 | 7/1973 | Lipcon et al. | 131/906 |
| 3,783,881 | 1/1974 | Lakos | 131/906 |
| 3,913,381 | 10/1975 | Heitmann | 73/37 |
| 3,968,904 | 7/1976 | Neville | 222/25 |
| 3,999,134 | 12/1976 | Lorenzen | 131/908 |
| 4,010,762 | 3/1977 | Strydom | 131/906 |
| 4,011,950 | 3/1977 | McLaughlin et al. | 209/73 |
| 4,045,657 | 8/1977 | Falke | 131/910 |
| 4,326,542 | 4/1982 | Laszlo et al. | 131/906 |
| 4,413,637 | 11/1983 | Irving | 131/84.1 |
| 4,503,868 | 3/1985 | Coyte | 131/907 |
| 4,548,215 | 10/1985 | Adebahr | 131/906 |
| 4,615,342 | 10/1986 | Federle et al. | 131/906 |

FOREIGN PATENT DOCUMENTS 1632208 8/1970 Fed. Rep. of Germany ...... 131/906

Primary Examiner—Robert Raevis
Attorney, Agent, or Firm—Peter K. Kontler

[57] ABSTRACT

The hardness of cigarettes which move in a direction at right angles to their axes is measured with one or more pivotable levers which rest on the moving cigarettes to elastically deform the adjacent portions of the cigarettes. The extent of elastic deformation is measured and the results of the measurements are used to regulate the operation of a cigarette rod making or filter tipping machine so as to ensure that the hardness of cigarettes will match an optimum value.

42 Claims, 4 Drawing Sheets

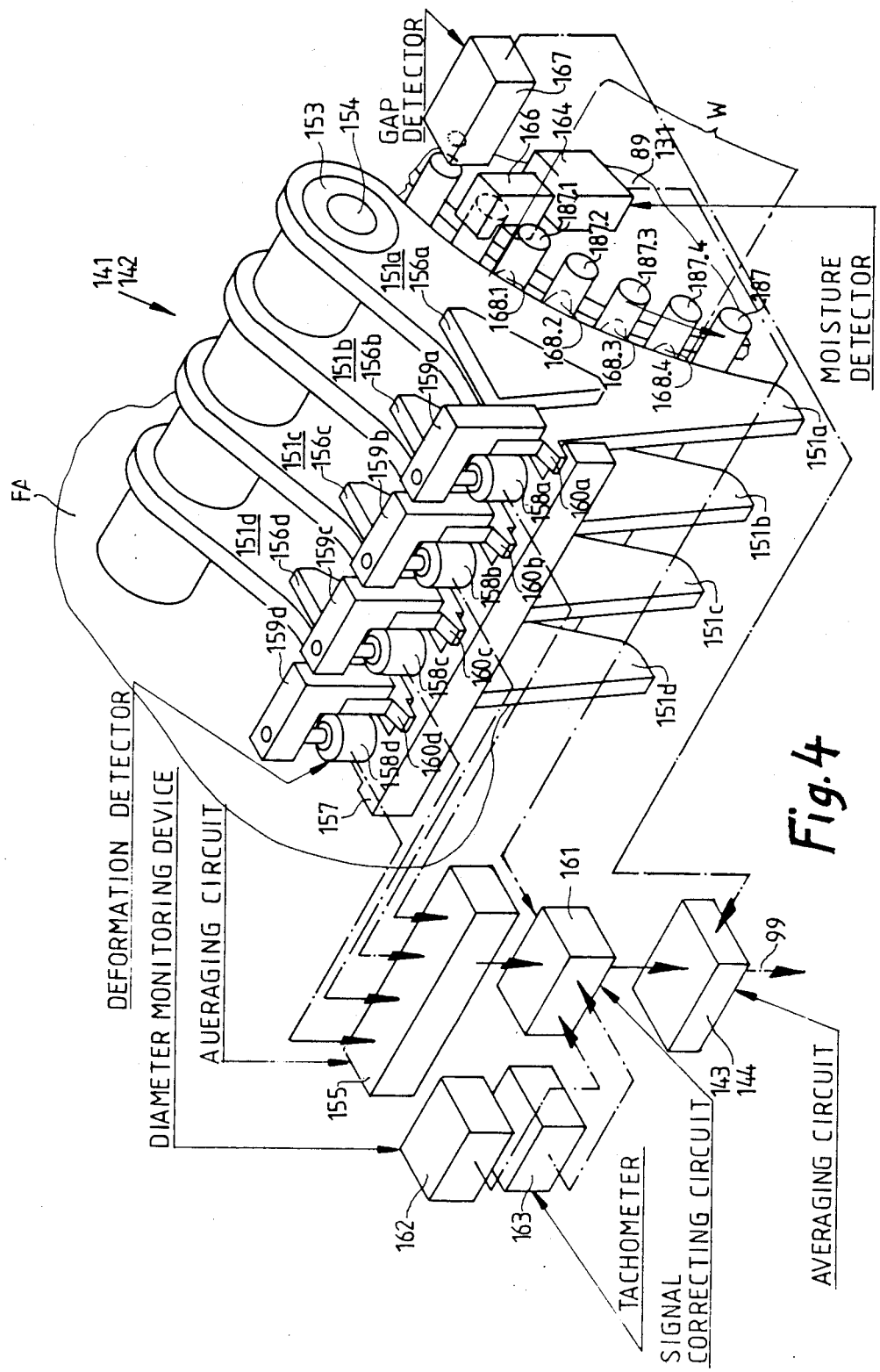

METHOD OF AND APPARATUS FOR ASCERTAINING THE HARDNESS OF CIGARETTES AND THE LIKE

This application is a continuation of application Ser. No. 261,840, filed Oct. 24, 1988 now abandoned.

BACKGROUND OF THE INVENTION

The invention relates to methods of and to apparatus for ascertaining certain parameters of fibrous material, particularly tobacco, and for using the results to influence the quality of products which contain the fibrous material. More particularly, the invention relates to improvements in methods of and in apparatus for determining the hardness of finished and/or incipient cigarettes and like rod-shaped products of the tobacco processing industry for the purpose of influencing the quality of such products and of reducing the number of rejects. Still more particularly, the invention relates to improvements in methods of and in apparatus for measuring certain parameters (such as hardness) of cigarettes or like rod-shaped products of the tobacco processing industry while the products are in motion in a rod making or filter tipping machine.

Hardness is a very important parameter of each rod-shaped product of the tobacco processing industry (such products will be called cigarettes or filter cigarettes for short with the understanding, however, that the method and apparatus of the present invention can be used with equal or similar advantage in connection with the making and processing of plain or filter cigars, cigarillos, cheroots and other rod-shaped products of the tobacco processing industry). Hardness denotes the resistance which the fibrous material of the filler in a cigarette offers to elastic deformation, particularly to deformation by the fingers of the smoker. Hardness of a cigarette is strongly influenced by the filling power of fibrous material which forms the filler, i.e., the rod-shaped condensed stream of tobacco particles which is surrounded by a tubular wrapper of cigarette paper or other suitable wrapping material. The term filling power denotes the ability of a given quantity of fibrous material (normally tobacco) to create the impression that the wrapper is properly filled with such material. Thus, a person holding a cigarette and not knowing the exact quantity of tobacco particles which fill the wrapper will gain the impression that the cigarette is plump and well rounded if the filling power of tobacco forming the filler is satisfactory, i.e., even if the wrapper confines a relatively small quantity of tobacco. Consequently, if the filling power of tobacco is rather high, the hardness of such product is also satisfactory to the smoker because a large majority of smokers prefer cigarettes which offer a certain amount of resistance to deformation. The hardness of cigarettes is monitored and the results of such monitoring operation are utilized to ensure that the hardness is increased if the tested products are too soft.

In accordance with a known proposal, a cigarette rod making machine is equipped with means for ascertaining the hardness of a continuous cigarette rod before the rod is subdivided into plain cigarettes of unit length or multiple unit length. It is also known to ascertain the filling power of the stream of tobacco particles which advance toward the wrapping (rod forming) station where the stream is draped into a continuous web of cigarette paper or other wrapping material to form therewith a continuous cigarette rod. Such determination of the filling power of a stream of tobacco particles involves the application of pressure in order to ascertain the resistance of the stream to deformation, i.e., to indirectly determine the hardness of cigarettes by actually ascertaining the filling power of tobacco which forms the stream. Indirect determination of hardness necessitates a determination of the mass flow of tobacco particles.

It is further known to indirectly ascertain the filling power of tobacco particles by measuring the height of the freshly formed tobacco stream ahead of the surplus removing (trimming or equalizing) station where one or more rotary and/or otherwise movable trimming members remove the surplus, and by also measuring the height of the equalized stream ahead of the wrapping station where the equalized stream is converted into the filler of a continuous cigarette rod. Instead of or in addition to measuring the height of the untrimmed and trimmed stream, it is also known to ascertain the filling power by monitoring the mass flow of the stream and/or the resistance which the stream offers to penetration of air or another gaseous fluid. The directly or indirectly gained results of such measurements of the filling power of tobacco particles and/or of the hardness of cigarettes are compared with reference values denoting the desired filling power and/or hardness, and the rod making machine is adjusted when the results of measurements depart from the reference value. The adjustment is intended to ensure that the filling power of tobacco particles and/or the hardness of cigarettes will at least closely approximate an optimum value, i.e., that such parameters of the fibrous material and of the rod-shaped products will remain at least substantially constant.

OBJECTS OF THE INVENTION

An object of the invention is to provide a novel and improved method of ascertaining the hardness of cigarettes and/or other rod-shaped products of the tobacco processing industry.

Another object of the invention is to provide a novel and improved of ascertaining the hardness of cigarettes and like products in such a way that the instrumentalities which are used to determine the hardness do not affect the appearance and/or other desirable characteristics of the products.

A further object of the invention is to provide a simple but reliable method which renders it possible to test the products at the rate at which such products issue from a mass producing machine, particularly a cigarette rod making or a filter tipping machine.

An additional object of the invention is to provide a novel and improved mode of utilizing the results of measurement of hardness of cigarettes or like products to influence the making of products with a view to reduce the number of rejects and to ensure that the quality of each product will match or closely approximate a desirable optimum value.

Still another object of the invention is to provide a novel and improved method of monitoring changes in the characteristics of cigarettes during treatment in a filter tipping machine.

A further object of the invention is to provide a novel and improved method of regulating the making of cigarettes, particularly of regulating the rate of removal of surplus from a tobacco stream which is about to be converted into the filler of a cigarette rod.

Another object of the invention is to provide a method which can be practiced with existing machines for the making and/or processing of rod-shaped smokers' products upon completion of relatively small alterations in the construction and/or mode of operation of such machines.

An additional object of the invention is to provide a novel and improved apparatus for ascertaining the hardness of cigarettes and like rod-shaped products of the tobacco processing industry.

A further object of the invention is to provide an apparatus which can be installed in or combined with existing cigarette making or processing machines.

Another object of the invention is to provide an apparatus which can ascertain the hardness of smokers' products at the same rate at which such products issue from a modern making or processing machine, which does not deface and/or otherwise affect the desirable characteristics of the products, and which can stand long periods of continuous use.

An additional object of the invention is to provide a production line for the making of smokers' products which embodies one or more hardness measuring apparatus exhibiting the aforediscussed characteristics.

Another object of the invention is to provide novel and improved means for evaluating and utilizing the results of measurement of hardness of cigarettes or other rod-shaped products of the tobacco processing industry.

A further object of the invention is to provide a novel and improved filter tipping machine.

Another object of the invention is to provide a novel and improved cigarette rod making machine.

An additional object of the invention is to provide novel and improved means for regulating the operation of the surplus removing device in a rod making machine.

A further object of the invention is to provide an apparatus which can influence the making of cigarettes or like rod-shaped articles of the tobacco processing industry in dependency upon two or more variable parameters, such as the hardness of the products, their diameters and their moisture content.

Another object of the invention is to provide a novel and improved circuit which processes signals from the improved hardness measuring apparatus.

SUMMARY OF THE INVENTION

One feature of the present invention resides in the provision of a method of ascertaining the hardness of cigarettes and like smokers' products which are capable of undergoing elastic deformation. The method comprises the steps of transporting the products sideways along at least one predetermined path, applying to the products a predetermined force so as to subject the products to elastic deformation, monitoring the extent of elastic deformation of the products, and generating signals which denote the extent of elastic deformation of the products. The signals are preferably electric signals.

The method can further comprise the steps of applying to the products at least one additional deforming force so as to subject the products to additional elastic deformation, monitoring the extent of additional elastic deformation of the products, generating additional signals denoting the extent of additional elastic deformation of the products, and converting the first named signals and the additional signals into further signals which denote average elastic deformation of the products. As mentioned above, the signals are preferably electric signals. The force of predetermined magnitude is applied to first portions of the products, and the additional force is applied to different additional portions of the products.

The transporting step can include conveying the products on a rotary endless conveyor, particularly on a drum having axially parallel peripheral flutes for the products. The products can be conveyed in the form of a series of successive products, and the force applying step can include simultaneously applying the force to at least two successive products of the series. The force can be a mechanical force or a force which is generated by a pressurized fluid. The mechanical force can be generated by one or more force applying members which engage the products by gravity and/or which are biased against the products by springs or by other suitable means.

If the transporting step takes place in a filter tipping machine wherein plain cigarettes, cigarillos or cigars are attached to filter rod sections, the force applying step can include the application of a first force in a first portion and the application of a second force (e.g., a force different from the first force) in a second portion of the path. For example, one of the forces can be applied to plain cigarettes immediately after or prior to entry into the filter tipping machine, and the other force can be applied to finished filter cigarettes.

The force applying step can include gradually increasing the magnitude of the force in a predetermined portion of the path, and such force applying step can further comprise gradually decreasing the magnitude of the force in a second portion of the path, preferably downstream of the first portion.

As mentioned above, the force applying step can include applying to the products the weight of a mechanical deforming member, particularly of a mechanical deforming member whose weight is constant.

If the products contain moisture which is likely to influence the results of the monitoring step, the method can further comprise the steps of monitoring the moisture content of the products, generating additional signals which denote the monitored moisture content of the products, and modifying the signals denoting the extent of elastic deformation of the products as a function of the additional signals.

If the products are rod-shaped, the method can further comprise the steps of monitoring the diameters of the products, generating additional signals which denote the monitored diameters of the products, and modifying the signals denoting the extent of elastic deformation of the products as a function of the additional signals.

The transporting step can include conveying the products in the form of a row which consists of a series of parallel products and normally has gaps as a result of randomly occurring absence of products. The force applying step can include applying to the products a force at intervals corresponding to the frequency of conveying successive products and gaps along a predetermined portion of the path, and the signal generating step then includes generating a signal during each of the aforementioned intervals. Such method preferably further comprises the step of processing only those signals which are generated as a result of elastic deformation of products in the predetermined portion of the path.

If the method serves to ascertain the hardness of products wherein a rod-like elastically deformable stream of fibrous material is draped into a web of wrapping material and the wrapped stream is subdivided into rod-shaped products each of which contains a portion of the stream, the method can further comprise the steps of monitoring at least one parameter of the portions of the stream prior to draping of the stream, generating additional signals which denote at least one parameter of the portions of the stream, and modifying the additional signals as a function of signals denoting the elastic deformation of corresponding products. The at least one parameter is the hardness of the portions of the stream or the filling power of fibrous material in the portions of the stream. The modifying step can include influencing the additional signals so as to maintain the hardness of the products within a predetermined range. The monitoring step can include directly or indirectly monitoring at least one parameter of the portions of the stream, e.g., directly or indirectly monitoring the height of the stream. Such monitoring step can include directing against the stream at least one beam of suitable radiation (such as corpuscular radiation or infrared rays) and ascertaining the quantity of radiation which penetrates through the stream. Alternatively, or in addition to monitoring with radiation, the monitoring step can include monitoring the mass flow of the material of the stream. Still further, the monitoring step can include directing against the stream at least one current of a gaseous fluid and ascertaining the extent of penetration of gaseous fluid through the stream.

Another feature of the invention resides in the provision of a method of testing cigarettes in filter tipping machines. Such method comprises the steps of delivering plain cigarettes to the machine, assembling plain cigarettes with filter rod sections in the machine to thus convert the plain cigarettes into filter cigarettes, monitoring the hardness of plain cigarettes prior to the assembling step, generating first signals which denote the hardness of the plain cigarettes, monitoring the signals denoting the hardness of filter cigarettes, and comparing the first signals with the corresponding second signals. Since the cigarettes are normally capable of undergoing elastic deformation, at least one of the monitoring steps can include transporting the cigarettes sideways (i.e., at least substantially at right angles to the axes of the cigarettes) and applying to the cigarettes a predetermined force so as to subject the cigarettes to elastic deformation. The corresponding monitoring step then includes monitoring the extent of elastic deformation of the cigarettes, and the corresponding signal generating step then comprises generating signals which denote the extent of elastic deformation of the cigarettes.

A further feature of the invention resides in the provision of a method of regulating the building of a stream of fibrous material, such as tobacco. The method comprises the steps of supplying fibrous material into a first portion of an elongated path, advancing the thus supplied fibrous material along the path in the form of a continuous stream, pneumatically attracting the stream to the path with a variable force, draping the stream into a web of wrapping material in a second portion of the path so as to form a rod wherein the web forms a tube around the stream, subdividing the rod into a series of discrete rod-shaped products, monitoring the hardness of the stream, generating signals which denote the monitored hardness, comparing the characteristics of the signals with the corresponding characteristics of a reference signal, and varying the attracting force when the monitored characteristics of the signals depart from the reference value.

The advancing step can include transporting the stream at one side of an endless foraminous conveyor, and the attracting step can include placing a suction chamber adjacent the other side of the conveyor or otherwise establishing a pressure differential between the sides of the conveyor so as to ensure that the stream is compelled to share the movements of the conveyor.

If the stream is elastically deformable, the monitoring step can include applying against successive portions of the stream a predetermined force so as to subject such portions of the stream to elastic deformation, monitoring the extent of elastic deformation of the stream portions, and generating signals which denote the extent of elastic deformation of the stream portions.

The varying step can include reducing the attracting force when the hardness of the stream increases and increasing such force when the hardness of the stream decreases.

The supplying step can include feeding or supplying fibrous material in such quantities or at such a rate that the stream contains a surplus of fibrous material. The method which involves the making of a stream with a surplus of fibrous material can further comprise the steps of equalizing the stream between the first and second portions of the path by removing at least some of the surplus at a location which is disposed at a variable distance from the path, and varying the distance of such location from the path when the monitored characteristics of the signals depart from the reference value.

The distance of the location of removal of the surplus from the stream can be varied also when the comparing step denotes the need for a variation of the force outside of a predetermined range so as to thereby maintain the hardness of the stream at a substantially constant value.

An additional feature of the invention resides in the provision of an apparatus for ascertaining the hardness of cigarettes and like smokers' products which are capable of undergoing elastic deformation. The apparatus comprises means for transporting the products sideways (i.e., substantially or exactly at right angles to their respective axes) along at least one predetermined path, means for applying to the products a predetermined force so as to subject the products to elastic deformation, and means for monitoring the extent of elastic deformation of the products including means for generating signals (preferably electric signals) which denote the extent of elastic deformation of the products. The force applying means can include at least one mechanical or fluid-operated force applicator which acts upon the products in a predetermined portion of the path.

It is often desirable and advisable to employ force applying means having a plurality of mechanical force applicators which are preferably adjacent each other and are operative to elastically deform different portions of transported products. The monitoring means of such apparatus can include a discrete monitoring device for each of the force applicators, and the signal generating means of such apparatus then includes means for generating discrete signals which denote elastic deformation of products by each of the mechanical force applicators. The monitoring means of such apparatus further comprises means for converting the discrete signals into further signals which denote average elastic deformation of the products.

The transporting means can include an endless conveyor, e.g., a rotary drum with axially parallel peripheral flutes for the products.

The force applying means can include at least one mechanical force applicator which serves to simultaneously deform a plurality of products in the path. The transporting means of such apparatus can comprise a conveyor which has means for advancing a series of successive parallel products along the at least one predetermined path. The applicator of the apparatus can include means for subjecting successive products of the series to the action of a progressively increasing deforming force in a predetermined portion of the path, and means for subjecting successive products of the series to the action of a progressively decreasing or diminishing deforming force in a second portion of the path, preferably downstream of the first portion.

In accordance with a presently preferred embodiment of the apparatus, the force applying means comprises at least one lever and means for pivotally mounting the lever so that the lever rests on the products in a predetermined portion of the path.

If the products contain moisture, the apparatus can further comprise means for monitoring the moisture content of the products including means for generating additional signals which denote the moisture content of the products, and means for modifying the signals denoting the extent of elastic deformation of the products as a function of the corresponding additional signals.

If the products are rod-shaped, the apparatus can further comprise means for monitoring the diameters of the products including means for generating additional signals which denote the diameters of the products, and means for modifying the signals denoting the extent of elastic deformation of the products as a function of the corresponding additional signals.

The transporting means can comprise means for conveying the products in the form of a row consisting of a series of parallel products and normally having gaps as a result of randomly occuring absence of products. The force applying means of such apparatus can comprise means for applying the predetermined force at intervals which correspond to the frequency of conveying successive products and gaps along a predetermined portion of the path so that the signal generating means generates a first signal during each of the intervals. The apparatus can further comprise means for monitoring the path for the presence of gaps including means for generating second signals which denote the presence of gaps, means for processing those first signals which denote the extent of deformation of products in the predetermined portion of the path, and means for preventing transmission to the processing mean of those first signals which are generated during intervals when the gaps are conveyed along the predetermined portion of the path.

If the apparatus is used to ascertain the hardness of smokers' products of the type wherein a stream of fibrous material is advanced along the path, the apparatus can further comprise means for supplying fibrous material into a first portion of the path so that the material is entrained by and forms a stream on the transporting means, means for draping the stream into a web of wrapping material in a second portion of the path downstream of the first portion so as to convert the stream and the wrapping material into a rod, means for subdividing the rod into a succession of rod-shaped products, means for monitoring a parameter of the stream upstream of the second portion of the path including means for generating additional signals which denote the monitored parameter, and means for modifying the additional signals as a function of signals which denote the extent of elastic deformation of the products. The aforementioned parameter can constitite the hardness of the stream or the filling power of the material of the stream.

Another feature of the invention resides in the provision of an apparatus for testing cigarettes in a filter tipping machine wherein plain cigarettes are united with filter rod sections to form filter cigarettes. The apparatus comprises means for transporting plain cigarettes and filter cigarettes sideways along a predetermined path, means for measuring or monitoring the hardness of plain cigarettes in a first portion of the path including means for generating first signals which denote the measured hardness of plain cigarettes, means for measuring or monitoring the hardness of filter cigarettes in a second portion of the path including means for generating second signals which denote the measured hardness of filter cigarettes, and means for comparing the first signals with the corresponding second signals.

Since a cigarette is normally deformable, at least one of the measuring means can include means for applying to cigarettes a predetermined force so as to subject the cigarettes to elastic deformation, and means for monitoring the extent of elastic deformation of cigarettes. The signals which are generated by the signal generating means of the one measuring means are then indicative of the extent of deformation of cigarettes.

Still another feature of the invention resides in the provision of an apparatus for regulating the building of a stream of fibrous material (such as tobacco). The apparatus comprises a foraminous conveyor which defines an elongated path and has a first side and a second side, a suction chamber which is located at one side of the conveyor, adjustable means for varying the pressure in the suction chamber, means for supplying fibrous material into a first portion of the path so that the thus supplied material forms a stream which advances along the path and is attracted to the other side of the conveyor as a result of the pressure differential which is established by suction chamber between the two sides of the conveyor, means for draping the stream into a web of wrapping material in a second portion of the path downstream of the first portion so that the stream and the wrapping material together form a continuous rod, means for subdividing the rod into products of predetermined length, means for monitoring a parameter (such as the hardness of the undraped stream, the hardness of the draped stream and/or the filling power of fibrous material of the stream) of the stream in the path and for generating signals which denote the monitored parameter, means for comparing the signals with a reference value, and means for adjusting the pressure varying means when the signals deviate from the reference value.

If the products are elastically deformable, the monitoring means can comprise means for applying to the products a predetermined deforming force so as to subject the products to elastic deformation. Such monitoring means further comprises means for monitoring the extent of elastic deformation of the products, and the signals are then indicative of the extent of elastic deformation of the products.

If the supplying means is designed to supply fibrous material at a rate such that the stream contains a surplus of fibrous material, the apparatus further comprises means for removing the surplus from the stream intermediate the first and second portions of the path at a variable distance from the other side of the conveyor, and means for varying the distance of the locus of removal from the other side of the conveyor in response to the signals so as to maintain the mass flow of material in the path at a substantially constant value.

The novel features which are considered as characteristic of the invention are set forth in particular in the appended claims. The improved apparatus themselves, however, both as to their construction and their mode of operation, together with additional features and advantages thereof, will be best understood upon perusal of the following detailed description of certain presently preferred embodiments with reference to the accompanying drawing.

BRIEF DESCRIPTION OF THE DRAWING

FIG. 4 is an enlarged perspective view of a presently preferred embodiment of the hardness measuring apparatus.

DESCRIPTION OF PREFERRED EMBODIMENTS

Figure 1:
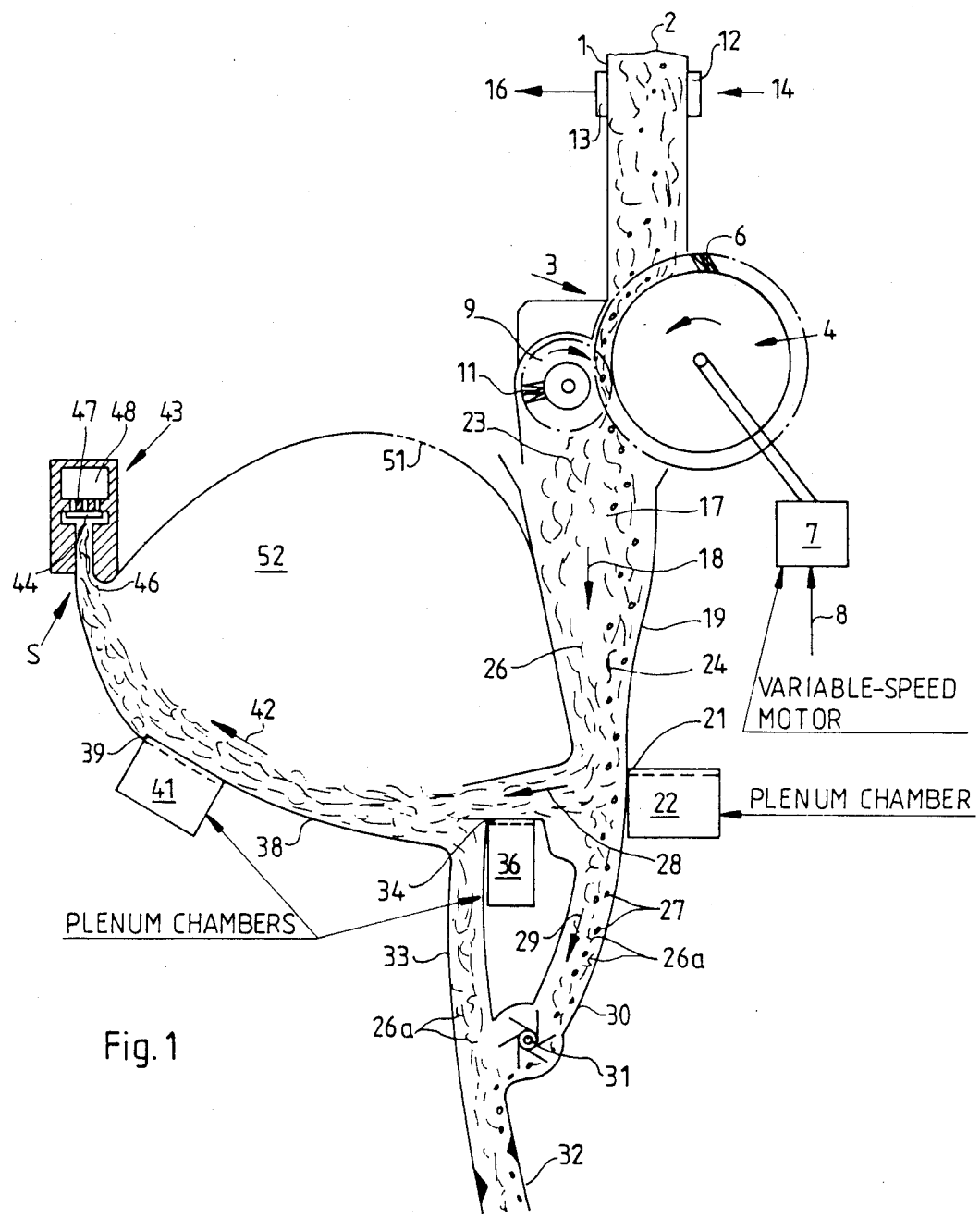
FIG. 1 is a schematic (partly end elevational and partly vertical sectional view) of a distributor in a cigarette rod making machine whose operation can be regulated in accordance with the method of the present invention.
Figure 2:
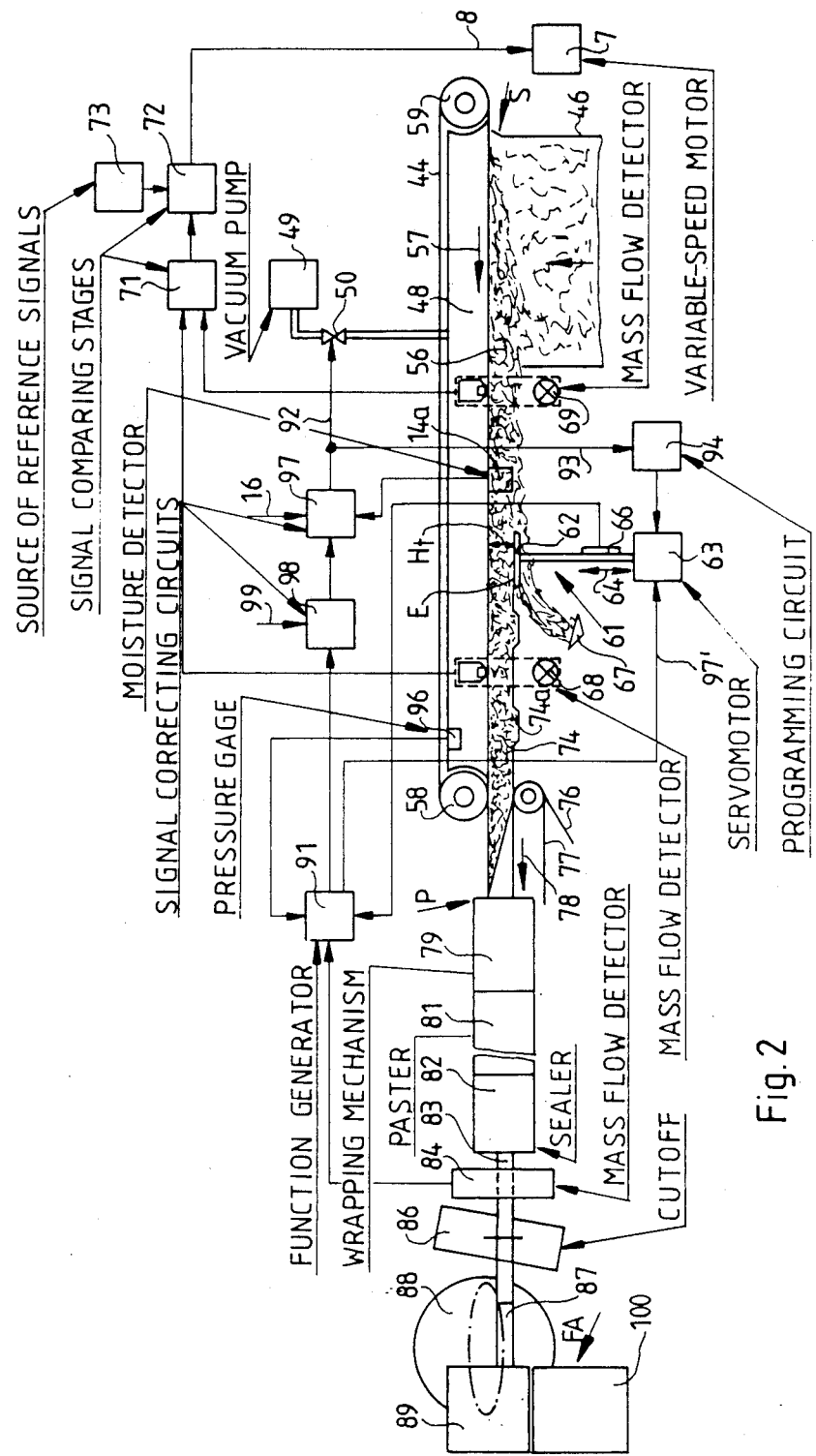
FIG. 2 is a schematic (partly elevational and partly vertical sectional view) of that portion of the rod making machine which receives fibrous material from the distributor of FIG. 1.

FIG. 1 shows the distributor (also called hopper) of a cigarette rod making machine of the type shown in FIG. 2. The distributor comprises an upright duct 1 which contains a column 2 of tobacco particles. The column 2 can contain natural tobacco, artificial tobacco and/or reconstituted tobacco and normally includes longer and shorter shreds as well as some fragments of tobacco ribs. The open lower end of the duct 1 is immediately adjacent a metering device 3 having a rotary drum-shaped conveyor 4 with a carding 6 which removes particles of tobacco from the lower end of the column 2 and advances them into the range of a rapidly rotating picker roller 9 having radially outwardly extending teeth 11 serving to expel tobacco particles from the carding 6 and to propel the expelled particles into the upper end portion of a funnel-shaped upright channel 19 wherein the particles form a shower 17 which descends in the direction of arrow 18. The conveyor 4 is driven by a variable-speed motor 7 (e.g., an electric motor) receiving signals (note the arrow 8) from the controls of a cigarette rod making machine which is shown in FIG. 2. The RPM of the picker roller 9 can greatly exceed the RPM of the conveyor 4.

The lower end of the channel 19 is adjacent a plenum chamber 22 having one or more nozzles 21 which discharge one or more jets of compressed air in the direction of arrow 28. This results in automatic classification of particles which form the shower 17. Thus, the lighter particles 23 (mainly shreds of tobacco leaf laminae) are propelled in the direction of arrow 28 whereas the heavier particles 27 (e.g., fragments of ribs) descend across the curtain of air which issues from the orifice or orifices of the nozzle(s) 21 and enter a downwardly extending duct 30 leading to a gate in the form of a rotary cell wheel 31. The direction in which the heavier particles 27 descend beneath the plenum chamber 22 is indicated by an arrow 29. The lighter particles 23 include relatively long shreds 24 and shorter shreds 26, and some of the shorter shreds (shown at 26a) are likely to be entrained by the heavier particles 27 so that they advance toward and are evacuated from the duct 30 to enter a further duct 32 serving for evacuation of heavier particles 27 from the distributor. The entrained shorter shreds 26a are salvaged in that they rise in an upwardly extending duct 33 under the injector effect of one or more nozzles 34 serving to discharge one or more jets of compressed air from a plenum chamber 36 adjacent the path of movement of lighter particles 24 and 26 in the direction of arrow 28.

The thus formed stream of lighter particles 24, 26 and 26a advances along a slightly upwardly sloping concave guide wall 38 in the direction of arrow 42 to be accelerated again by one or more jets of compressed air issuing from one or more nozzles 39 which receive compressed air from a plenum chamber 41. Successive increments of the stream reach the underside of the lower reach of a foraminous endless belt conveyor 44 (see also FIG. 2) forming part of a transporting unit 43 which advances the stream along an elongated substantially horizontal path in a direction at right angles to the plane of FIG. 1. The lower reach of the conveyor 44 constitutes the top wall of an elongated tobacco channel 46. The transporting unit 43 further comprises a suction chamber 48 which has a perforated bottom wall 47 adjacent the upper side of the lower reach of the conveyor 44 so that the suction chamber establishes a pressure differential between the upper side and the underside of the lower reach of the conveyor 44 and thus ensures that the particles of the stream are attracted to and share the movement of the lower reach. 5. FIG. 2 shows that the suction chamber 48 is disposed between the upper and lower reaches of the conveyor 44 and is connected with a suitable suction generating device 49 (e.g., a vacuum pump) by a conduit containing an adjustable regulating valve 50 constituting a means for varying the pressure in the suction chamber 48 in order to change the extent to which the particles 24, 26 and 26a are compacted as a result of upward flow of air through the growing stream 56 of tobacco particles at the underside of the lower reach of the conveyor 44. Such lower reach advances in the direction of arrow 57.

The surplus of air which issues from the plenum chambers 22, 36 and 41 of FIG. 1 gathers in an expansion chamber 52 and is evacuated by way of a sieve 51. Reference may be had to numerous United States and foreign patents of the assignee of the present application.

FIG. 1 further shows that the duct 1 for the column 2 of tobacco particles therein is flanked by two electrodes 12 and 13 forming part of a capacitive moisture measuring device 14 of known design. Suitable moisture measuring devices are produced by the assignee of the present application. The arrow 16 denotes the output for transmission of signals which denote the monitored or measured moisture content of tobacco particles forming the column 2. The means for evaluating signals from the moisture measuring device 14 forms part of the control circuit for the rod making machine of FIG. 2.

The endless foraminous belt conveyor 44 of the transporting unit 43 is trained over pulleys 58, 59 (FIG. 2) at least one of which is driven so as to advance the lower reach of the conveyor 44 in the direction of arrow 57. The particles 24, 26 and 26a which form the stream are supplied into the channel 46 to form a growing stream which is fully grown (the fully grown stream is shown at 56) at the left-hand end of the channel 46 and advances with the lower reach of the conveyor 44 toward a surplus removing or equalizing station where the surplus 67 of fibrous material is removed by a vertically adjustable trimming device 61. The latter can comprise two substantially coplanar trimming or clamping discs 62 which are driven to rotate about substantially vertical axes and clamp the stream 56 at a selected level so that the surplus 67 is located beneath the plane of the discs 62. A paddle wheel, a rotary brush or another suitable tool (not shown) is provided to sweep away the surplus 67, and the thus removed surplus is readmitted into the distributor of FIG. 1, e.g., onto the guide wall 38 downstream of the nozzle or nozzles 34 so that the recirculated surplus 67 need not be subjected to a renewed classifying action in the channel 19.

The plane in which the device 61 trims the surplus-carrying stream 56 is shown at E, and the distance of this plane from the underside of the lower reach of the conveyor 44 is shown at Ht. The means for varying the distance Ht includes an adjustable servomotor 63 which can move the discs 62 and the aforementioned surplus removing tool in directions indicated by a double-headed arrow 64, i.e, nearer to or further away from the lower reach of the conveyor 44. A distance monitoring device 66 of any known design is provided to generate signals denoting the actual distance Ht of the trimming discs 62 from the lower reach of the conveyor 44.

It is also possible to vary the distance Ht by employing a trimming device whose level is fixed and by moving the lower reach-of the conveyor 44 toward the discs 62 of such fixedly mounted trimming device. The monitoring device 66 is then replaced by a device which can transmit signals denoting the level of the lower reach of the conveyor 44.

The rod making machine of FIG. 2 employs a first measuring or monitoring device 68 which ascertains the mass flow of tobacco particles downstream of the trimming station, and a second measuring or monitoring device 69 which ascertains the mass flow of tobacco particles upstream of the trimming station but downstream of the stream building or growing zone S. Each of the measuring devices 68, 69 can comprise a radiation source (preferably a source of infrared light) at one side of the path for the stream 56 and an optoelectronic transducer (e.g., a diode) at the other side of such path opposite the respective radiation source so as to ascertain the quantity of radiation which penetrates through the stream and to generate a signal denoting the quantity. Such types of measuring or monitoring devices are described in numerous pending patent applications of the assignee of the present application. The trimmed or equalized stream is shown at 74; this stream can have uniformly spaced-apart raised portions 74a which contain larger quantities of tobacco particles and are disposed at the ends of cigarettes 87 which are produced in the machine of FIG. 2 so that the cigarettes are provided with so-called dense ends to reduce the likelihood of escape of tobacco particles during further processing of cigarettes or during smoking.

The transducers of the measuring devices 68 and 69 transmit signals to a signal comparing stage 71 which transmits a signal denoting the difference of the received signals and thus denoting the mass flow of tobacco particles in the removed surplus 67. The signal at the output of the comparing stage 71 is transmitted to one input of a second signal comparing stage 72. A second input of the stage 72 receives reference signals from a source 73 (e.g., an adjustable potentiometer), and the output 8 of the stage 72 transmits a signal to the motor 7 to alter the speed of the carded conveyor 4 in the distributor of FIG. 1 when the characteristics of signals from the stage 71 depart from the characteristics of reference signal from the source 73. The adjustment of the motor 7 in response to signals from the output 8 of the stage 72 is such that the mass flow of tobacco particles which form the removed surplus 67 is at least substantially constant.

The equalized stream 74 is advanced to a wrapping station P where successive increments of this stream are condensed in a conventional wrapping mechanism 79 and are draped into successive increments of a continuous web 76 of cigarette paper or another suitable wrapping material which is drawn off a reel (not shown) and is advanced in the direction of arrow 78 by the upper reach of an endless belt conveyor 77 (called garniture belt). One marginal portion of the partially draped web 76 is coated with a film of adhesive in a paster 81, and such marginal portion is then folded over the other marginal portion to form a customary seam extending in parallelism with the axis of the thus obtained continuous cigarette rod 83. A so-called sealer 82 is provided downstream of the paster 81 to promote the setting of adhesive in order to ensure that the seam will not open during severing of the rod 83 by a customary cutoff 86 which converts the rod into a file of discrete rod-shaped products (plain cigarettes) 87 of unit length or multiple unit length. The height of the untrimmed stream 56, the height of the trimmed stream 74 and the diameter of the rod 83 are exaggerated in FIG. 2 for the sake of clarity.

The mass flow of tobacco particles in the filler (equalized and condensed stream 56) of the cigarette rod 83 is monitored by a detector 84 which can comprise a source of corpuscular radiation (e.g., beta rays) at one side of the path of the rod 83 and a suitable transducer (e.g., an ionization chamber) at the other side of the path opposite the radiation source. The transducer generates signals which denote the percentage of radiation that has penetrated through the rod 83, and such signals are transmitted to a function generator 91. Signals which are transmitted by the transducer of the detector 84 denote the mass flow of tobacco particles in the rod 83 as well as the mass flow of tobacco particles in the trimmed or equalized stream 74.

Successive cigarettes 87 or successive pairs of cigarettes 87 are taken over by an intermediate conveyor 88 which transfers such cigarettes onto a conveyor 89 (see also FIG. 3) of a filter tipping machine FA. The conveyor 88 can be of the type disclosed in commonly owned U.S. Pat. No. 4,051,947 granted Oct. 4, 1977 to Schumacher et al. for "Transfer apparatus for cigarettes or the like". The purpose of the conveyor 88 is to change the direction of advancement of cigarettes 87; thus, the cigarettes 87 which leave the cutoff 86 of FIG. 2 in the form of a single file (i.e., which move axially) are converted into one or more row whose constituents move sideways (namely at right angles to their respective axes). The conveyor 89 is an endless drum-shaped conveyor and it delivers successive plain cigarettes of one or more rows to the axially parallel peripheral flutes of a second rotary drum-shaped conveyor 100 in the filter tipping machine FA.

The function generator 91 of FIG. 2 receives signals from the transducer of the detector 84, from a pressure monitoring device 96 in the suction chamber 44, and from the distance monitoring device 66. The manner in which the function generator 91 processes (preferably amplified) signals from the detector 84 and device 66 into signals denoting the filling power of tobacco particles in and/or the hardness of the trimmed stream 74 is fully disclosed in commonly owned U.S. Pat. No. 4,280,516 granted July 28, 1981 to Reuland for "Method and apparatus for producing a continuous filler of tobacco or the like". Signals which are transmitted by the function generator 91 are also indicative of the hardness of the cigarette rod 83 and hence of the plain cigarettes 87. The patent to Reuland further discloses that signals from the function generator 91 can be used to change the distance Ht (the level of the trimming device 61) as a result of appropriate adjustment of the servomotor 63 (note the conductor 97 in FIG. 2). In addition, an output of the function generator 91 serves to transmit signals to the valve 50 (this is not disclosed by Reuland) so as to vary the pressure in the suction chamber 48 and hence the extent to which the stream 56 is compacted during travel with the lower reach of the conveyor 44. The pressure monitoring device 96 transmits to the function generator 91 signals denoting the actual pressure in the suction chamber 48 so that the adjustment of the valve 50 can be terminated as soon as the pressure reaches a desired value.

The reason for adjustability of valve 50 (and hence of the pressure in the suction chamber 48) is that, when the signal at the output of the function generator 91 indicates a reduction of hardness of the rod 83 and a reduction of the filling power of the fibrous material therein (such signal is a function of the mass flow and of the distance Ht), the pressure in the chamber 48 should be increased. This is effected by the signal which is transmitted from the function generator 91 to the valve 50 via conductor 92. At the same time, a conductor 93 transmits such signal to a programming circuit 94 which selects the level of the trimming device 61 via servomotor 63 in accordance with a program so that the distance Ht of the trimming plane E from the lower reach of the conveyor 44 is increased simultaneously with a reduction of suction (rise of pressure) in the suction chamber 48. Such movement of the trimming device 61 away from the conveyor 44 is desirable because when the pressure in the chamber 48 rises, the stream 56 expands toward the trimming device 61 because the pressure differential between the upper side and the underside of the lower reach of the conveyor 44 is reduced. A lowering of the plane E at such time ensures that the trimming device 61 cannot remove excessive quantities of tobacco which would result in a further reduction of hardness of the rod 83 and cigarettes 87. As mentioned above, the same result can be achieved if the trimming device 61 is fixedly mounted at a given level and the signal from the programming circuit 94 causes a servomotor or the like to raise or lower the level of the lower reach of the conveyor 44.

When the pressure monitoring device 96 transmits to the function generator 91 a signal which denotes that the pressure in the suction chamber 48 has risen to a predetermined level which should not be exceeded (i.e., that suction in the chamber 48 has dropped to a minimum permissible level), the function generator 91 does not initiate a further drop of suction in the chamber 48; instead, the function generator 91 transmits a signal via conductor 97' so that the servomotor 63 increases the distance Ht of the trimming device 61 from the conveyor 44 with the result that the quantity of surplus 67 is reduced and the trimmed stream 74 contains a larger quantity of tobacco particles per unit length. Therefore, the hardness of the rod 83 and of the cigarettes 87 remains constant or increases.

If the function generator 91 ascertains that the hardness of the rod 83 and of the cigarettes 87 is excessive, the signal which is transmitted via conductor 92 causes the valve 50 to effect a reduction of pressure in the suction chamber 48 so that compacting action of air flowing upwardly through the stream 56 increases. At the same time, the programing circuit 94 causes the servomotor 63 to reduce the distance Ht and to thus ensure that the mass flow remains at least substantially constant. When the pressure in the suction chamber 48 drops to a predetermined minimum acceptable value but the hardness of the rod 83 is still excessive, the pressure in the chamber 48 is not reduced but the function generator 91 transmits a signal via conductor 97 in order to reduce the distance Ht by raising the trimming plane E, i.e., to reduce the quantity of fibrous material per unit length of the untrimmed stream 56 and trimmed stream 74.

If the moisture content of tobacco particles fluctuates, such fluctuations can distort the signals which denote the hardness of the rod 83 and cigarettes 87. The reason is that an increasing moisture content of the material of the stream 56 creates the impression of a reduced hardness and a decreasing moisture content creates the impression of more pronounced hardness of the rod 83. The means which compensates for such influence of moisture content of tobacco particles upon those signals which should influence the pressure in the suction chamber 48 and/or the level of the trimming plane E includes a signal correcting or influencing circuit 97 which receives the signals from the output 16 of the moisture measuring device 14 of FIG. 1. The circuit 97 influences signals which are transmitted to the valve 50 (conductor 92) and to the programming circuit 94 (conductor 93) so as to prevent the moisture content of tobacco particles which are to form the stream 56 from adversely influencing the signals denoting the ascertained hardness of the rod 83 and cigarettes 87.

An advantage of placing the capacitive moisture measuring device 14 next to the duct 1 is that there is ample room for relatively large electrodes 12 and 13 which ensures that signals which are transmitted by the output 16 accurately reflect the actual moisture content of tobacco particles in the monitored zone of the duct 1.

In addition to or in lieu of the moisture measuring device 14 adjacent the duct 1, the rod making machine of FIG. 2 can employ a moisture measuring device 14a which is installed adjacent or in the path of movement of the stream 56 with the lower reach of the conveyor 44 and the output of which is connected with a corresponding input of the signal influencing or correcting circuit 97. The manner in which the moisture measuring device 14a can influence signals denoting the density of a tobacco stream is fully disclosed in the aforementioned Reuland U.S. Pat. No. 4,280,516. The measuring device 14a exhibits the advantage that it is close to the locus or loci of monitoring the stream 56 for the purpose of ascertaining its density. This ensures that eventual changes of moisture content of tobacco particles between the duct 1 and the path portion immediately upstream of the trimming or equalizing station do not remain undetected and can be taken into consideration in adjusting the valve 50 and/or the servomotor 63 for the trimming device 61. If the machine of FIG. 2 employs the moisture measuring device 14, the conductor from the output 16 of such device to the signal correcting circuit 97 (or the circuit 97) can contain a suitable signal delaying component, e.g., a shift register, to ensure that the output 16 transmits to the correcting circuit 97 signals denoting the moisture content of those increments of the column 2 which form part of the stream 56 at the trimming station.

A further signal correcting circuit 98 is installed in the conductor 92 between the function generator 91 and the valve 50 ahead of the signal correcting circuit 97. An input of the signal correcting circuit 98 receives signals via conductor means 99 from a novel hardness ascertaining apparatus of the type shown in FIG. 4. Signals which are transmitted via conductor means 99 are more reliable (i.e., more accurate) than the relatively rapidly obtained signals which are generated in the function generator 91 and are indicative of hardness of the rod 83 and cigarettes 87. Signals which are transmitted via conductor means 99 are generated as a result of measuring the hardness of plain cigarettes 87 in the filter tipping machine FA of FIG. 3, i.e., these signals are generated with a certain delay following advancement of fibrous material which is to form the fillers of cigarettes 87 past the trimming station. Therefore, it is normally desirable to regulate the hardness on the basis of potentially less accurate but immediately available hardness-indicating signals which are transmitted by the function generator 91, and to correct such potentially less accurate signals as a function of signals which the correcting circuit 98 receives via conductor means 99. Such modification of signals from the function generator 91 to the valve 50 and to the programming circuit 94 reduces the likelihood or possibility of long-range deviations of the characteristics of signals which are transmitted by the function generator 91 from values accurately reflecting the hardness of the stream 74, i.e., the signal correcting circuit 98 ensures that the rod making machine of FIG. 2 cannot turn out a long series of rejects.

Figure 3:
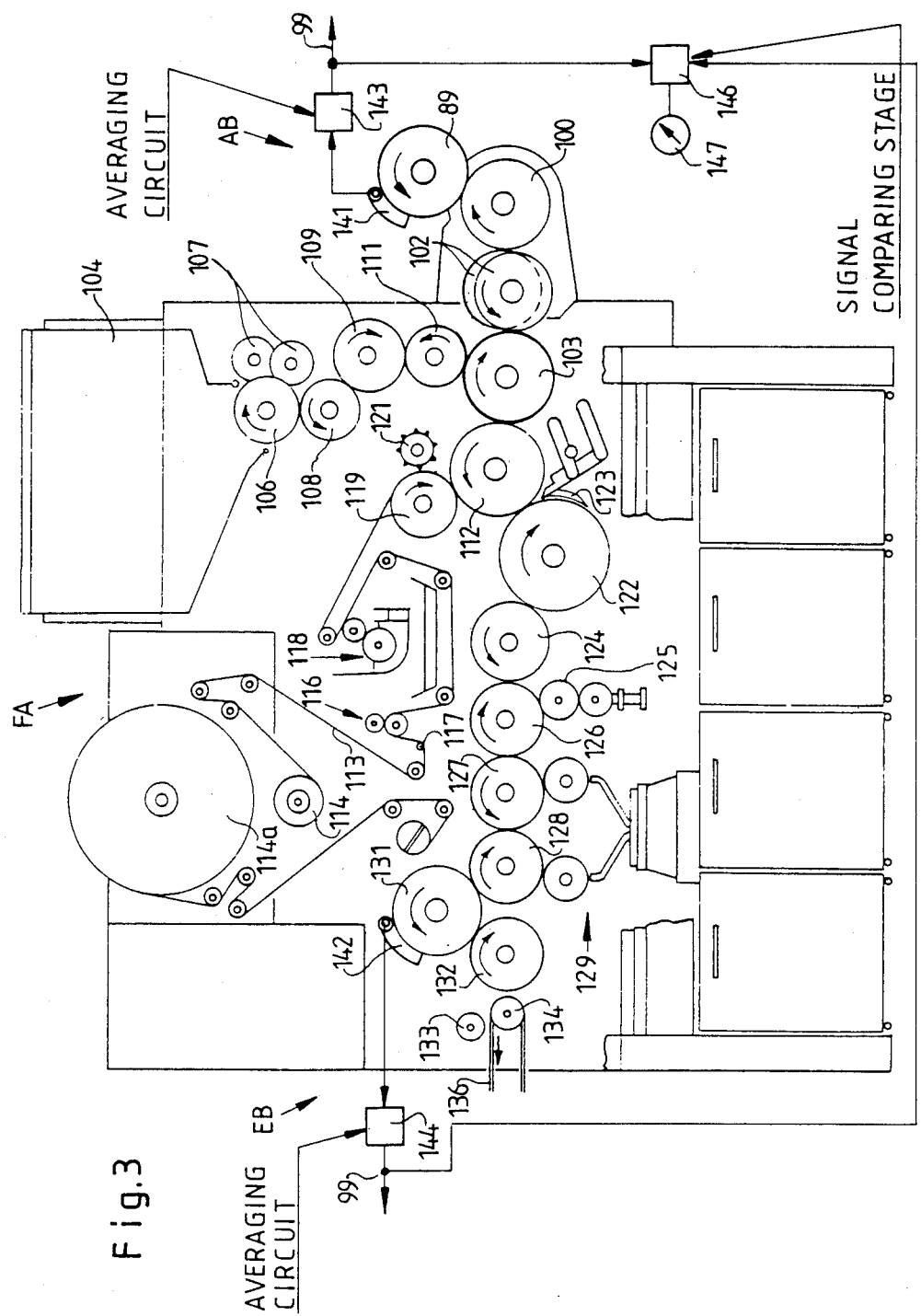
FIG. 3 is a schematic front elevational view of a filter tipping machine which embodies two hardness measuring apparatus.

FIG. 3 shows a filter tipping machine FA which embodies or cooperates with two hardness ascertaining apparatus of the type shown in FIG. 4. The aforementioned drum-shaped conveyor 89 of the filter tipping machine FA constitutes a means for transporting plain cigarettes 87 sideways along a predetermined path which extends through the first hardness ascertaining or testing station at the inlet of the filter tipping machine. As already mentioned above, the conveyor 89 delivers plain cigarettes 87 to successive flutes of the conveyor 100 which, in turn, delivers alternating cigarettes 87 to two discrete rotary drum-shaped conveyors 102 which transport the thus received cigarettes at different speeds and/or through different distances so as to ensure that each axially parallel peripheral flute of an assembly conveyor 103 receives a pair of coaxial plain cigarettes 87 with a gap between them so as to provide room for insertion of a filter rod section or filter plug of double unit length.

A magazine 104 on top of the frame of the filter tipping machine FA contains a supply of parallel filter rod sections of six times unit length. Such filter rod sections are caused to enter the axially parallel peripheral flutes of a severing conveyor 106 which cooperates with two axially staggered rotary disc-shaped knives 107 to subdivide each filter rod section of six times unit length into three coaxial filter rod sections or filter plugs of double unit length. Groups of three coaxial filter plugs are transferred onto the rotary components of a staggering conveyor 108 which delivers the thus staggered filter plugs into successive flutes of an aligning or shifting conveyor 109 cooperating with one or more cams serving to shift some or all of the filter plugs of double unit length axially in order to form a single row wherein each next-following filter plug is in exact alignment with all preceding filter plugs. Successive filter plugs of such single row are transferred into successive flutes of a combined accelerating and inserting conveyor 111 which places filter plugs of double unit length between successive pairs of spaced-apart but coaxial plain cigarettes 87 in the flutes of the assembly conveyor 103. The thus obtained groups of three coaxial rod-shaped products each (namely two plain cigarettes 87 and a filter plug of double unit length between them) are delivered into the flutes of a rotary drum-shaped transfer conveyor 112 which accepts adhesive-coated uniting bands from a rotary drum-shaped suction conveyor 119 cooperating with a rotary drum-shaped cutter 121. The transfer conveyor 112 cooperates with one or more stationary cams or other suitable condensing means serving to move one or both plain cigarettes 87 of each group axially toward the respective filter plug so as to ensure that the inner ends of plain cigarettes actually abut the respective ends of the filter plug between them.

The frame of the filter tipping machine FA supports a mandrel for the core of an expiring reel 114 serving to pay out a web 113 of tipping paper. The web 113 is drawn off the core of the expiring reel 114 by two advancing rolls 116 which cooperate with the suction conveyor 119 to advance the web 113 along a predetermined path extending through a paster 118 wherein one side of the web is coated (at least in part) with a suitable adhesive. The leader of the web 113 is severed at regular intervals by the blades of the rotary cutter 121 (the conveyor 119 can be said to constitute an anvil for the blades of the cutter 121) so that the web 113 yields a series of discrete adhesive-coated uniting bands each of which is affixed to the oncoming group of coaxial rod-shaped products in such a way that the uniting band extends tangentially of the group and is in substantial linear contact with the respective filter plug of double unit length as well as with the adjacent inner end portions of the respective plain cigarettes 87.

FIG. 3 further shows a conventional stress equalizing device 117 which is adjacent the path of the web 113 upstream of the advancing rolls 116 and has a sharp edge serving to eliminate or equalize internal stresses in the web 113. A spare reel 114a of tipping paper is supported by the frame of the tipping machine FA in a position of readiness to have the leader of the spare web spliced to the trailing end of the web 113 when the supply of tipping paper on the reel 114 is nearly exhausted.

The transfer conveyor 112 delivers successive groups of rod-shaped articles and the corresponding uniting bands to a rolling conveyor 122 which cooperates with a stationary but preferably adjustable rolling device 123 so as to convolute each uniting band around the respective filter plug and around the adjacent inner end portions of the respective plain cigarettes 87 in order to convert the groups into filter cigarettes of double unit length. Each converted uniting band then forms a tube which sealingly connects the respective filter plug of double unit length to the adjacent plain cigarettes.

A heated conveyor 124 accepts successive filter cigarettes of double unit length from the rolling conveyor 122 and ensures immediate or rapid setting of the adhesive which was applied by the paster 118. The thus treated filter cigarettes of double unit length are transferred to a severing conveyor 126 cooperating with a rotary disc-shaped knife 125 to form pairs of coaxial filter cigarettes of unit length by severing each filter cigarette of double unit length midway between the respective plain cigarettes. Each filter cigarette of unit length contains a plain cigarette 87 of unit length, a filter plug of unit length and a tube (converted uniting band) of unit length. Defective filter cigarettes of unit length are segregated from satisfactory filter cigarettes before the satisfactory filter cigarettes leave the conveyor 126.

Pairs of filter cigarettes of unit length are transferred onto a rotary drum shaped conveyor 127 of a turn-around device 129 of the type disclosed in commonly owned U.S. Pat. No. 3,583,546 granted June 8, 1987 to Koop for "Apparatus for inverting cigarettes or the like." The purpose of the device 129 is to turn one filter cigarette of each pair end for end so that the filter plugs of all filter cigarettes of unit length face in the same direction not later than on the drum-shaped conveyor 128 of the device 129 as well as that the inverted filter cigarettes alternate with the non-inverted filter cigarettes. Successive filter cigarettes of the thus obtained single row of filter cigarettes are delivered into successive flutes of a rotary drum-shaped conveyor 131, forming part of a second hardness measuring or ascertaining apparatus 142.

The conveyor 131 is followed by a conveyor 132 which is provided with or cooperates with means for segregating filter cigarettes of unacceptable hardness from satisfactory cigarettes and delivers satisfactory filter cigarettes onto an endless belt conveyor 136 trained over pulleys 134 (only one shown) and cooperating with a rotary braking device 133. The discharge end of the belt conveyor 136 delivers a row of satisfactory filter cigarettes of unit length into storage (e.g., into a reservoir of the type known as RESY and described in numerous United States and foreign patents of the assignee of the present application) or directly to a packing machine.

The conveyor 132 can further comprise or cooperate with means for monitoring the density of the tobacco-containing ends of filter cigarettes of unit length. Save for the provision of the two hardness ascertaining apparatus 141 and 142, the filter tipping machine FA may be of the type known as MAX or MAX S both produced and distributed by the assignee of the present application and described in numerous United States and foreign patents of the assignee.

The two hardness measuring or ascertaining apparatus 141, 142 are or can be of identical design. FIG. 4 shows the details of one of these apparatus. The conveyor 89 or 131 forms part of the respective transporting unit which advances plain cigarettes 87 (conveyor 89) of filter cigarettes 187 (conveyor 131) sideways (i.e., at right angles to their respective axes) in the course of the measuring or ascertaining operation. The apparatus 141 and 142 respectively comprise averaging circuits 143, 144 which transmit signals via conductor means 99 to the signal correcting circuit 98 of FIG. 2. Signals at the outputs of the averaging circuits 143, 144 are indicative of hardness of the respective (plain and filter) cigarettes 87, 187 and are modified as a function of other signals denoting various parameters which are likely to distort the signals from the respective hardness ascertaining apparatus. These parameters are the moisture content of tobacco, the diameters of the rod-shaped products and the speed at which the products are transported past the respective testing stations. Moreover, the circuits 143, 144 average the signals which are obtained as a result of testing of a predetermined number (e.g., 100 to 150) cigarettes. Signals from the averaging circuits 143, 144 are transmitted to a signal comparing stage 146 which compares the signals and transmits an output signal which is indicative of the difference. Such signal can be displayed on the dial of a gauge 147 or otherwise and denotes the difference between the monitored hardness at the inlet end AB (apparatus 141) and outlet end EB (apparatus 142) of the filter tipping machine FA of FIG. 3. The information which is supplied at 147 can be used to determine the mode of operation of the machine FA and to carry out all necessary corrections so as to reduce the number of rejects and to ensure that the quality of each filter cigarette 187 of unit length will match or closely approximate an optimum value. If necessary or desirable, signals which are supplied by the signal comparing stage 146 can be used to determine the extent of changes of hardness of rod-shaped products which are brought about by the rolling conveyor 122 in conjunction with the rolling member 123.

Signals which are transmitted by the apparatus 141 or 142 can be transmitted to the signal correcting circuit 98 of FIG. 2 in order to correct signals from the function generator 91 because the signals from the apparatus 141 or 142 are more reliable than those which are obtained as a result of determination of hardness of the rod 83 and/or plain cigarettes 87 on the basis of measurements at 84. The designer of the rod making machine of FIG. 2 will decide to connect the signal correcting circuit 98 with the apparatus 141 if the changes of hardness taking place during travel of plain cigarettes 87 through the filter tipping machine FA are to be disregarded. It is also possible to connect the signal correcting circuit 98 with the output of the signal comparing stage 146.

Referring to FIG. 4, the hardness measuring or ascertaining apparatus 141 or 142 comprises a force applying unit including several force applicators in the form of levers 151a, 151b, 151c and 151d. These levers are pivotally mounted for angular movement about the axis of a shaft 154 which is mounted in the frame of the tipping machine FA and the weight of the levers 151a-151d rests on the adjacent cigarettes (hereinafter referred to as filter cigarettes) 187.1, 187.2, 187.3 and 187.4 in the axially parallel peripheral flutes of the drum-shaped conveyor 131. The levers 151a-151d are assumed to be rotatable relative to the shaft 154 and are mounted on antifriction bearings (e.g., ball bearings) 153 so that they can readily turn about the axis of the shaft 153.

The configuration of the undersides of the levers 151a-151d is such that they hardly contact the respective portions of a filter cigarette 187.1 which has just entered the testing station so that such filter cigarette is subjected to slight elastic deformation under the weight of the adjacent portions of the levers. The deforming force thereupon increases gradually to a maximum value (note the filter cigarettes 187.2 and 187.3 which precede the filter cigarette 187.1). The next-following portions of the levers 151a–151d thereupon bring about a gradually decreasing deforming action (note the filter cigarette 187.4 which immediately precedes the filter cigarette 187.3 in the direction of (counterclockwise) rotation of the conveyor 131). The testing region where the filter cigarettes 187.1 to 187.4 are acted upon by all four levers 151a–151d is shown at W. The filter cigarette which is denoted by the character 187 has already advanced beyond the testing region W.

The levers 151a–151d are provided with preferably detachable and exchangeable weights 156a, 156b, 156c, 156d which can be applied, removed or replaced with other weights in order to select the force with which the levers act upon and elastically deform the filter cigarettes in the testing region W.

The means for monitoring the extent of elastic deformation of filter cigarettes 187.1 to 187.4 in the testing region W is mounted on a support 157 (which is installed in the frame of the filter tipping machine FA) and includes conventional inductively operated detectors 158a, 158b, 158c, 158d which comprise armatures (not shown) adapted to be shifted by projections 159a, 159b, 159c, 159d of the respective levers 151a–151d. Suitable inductively operating detectors are offered for sale under the designation MTK 2 in the brochure "Induktive Wegaufnehmer" (10/83) of the Company Messring, D-8000 Munich, P.O. Box 40 06 660, Federal Republic of Germany. The extent to which the armatures are shifted is indicative of the average extent of deformation of filter cigarettes by the respective levers.

The levers 151a–151d further respectively comprise protuberances 160a, 160b, 160c, 160d which are free to engage the support 157 when the series of filter cigarettes in the flutes of the conveyor 131 develops a gap as a result of the absence of one or more cigarettes. These protuberances protect the levers 151a–151d and the conveyor 131 from excessive wear by preventing the levers from actually engaging the rotating conveyor 131 when the apparatus 142 is in use but filter cigarettes are lacking in the testing region W where the levers 151a–151d are supposed to elastically deform predetermined numbers of successive filter cigarettes in a simultaneous operation.

The filter cigarettes are attracted to the surfaces bounding the respective flutes of the conveyor 131 first by suction (the surfaces bounding the flutes are provided with suction ports which are not shown in FIG. 4) and thereupon (in the testing region W) by ring-shaped elastic retaining elements of the type disclosed in commonly owned U.S. Pat. No. 4,528,841 granted July 16, 1985 to Siems for "Apparatus for testing cigarettes and the like".

Signals which are generated by the detectors 158a–158d are transmitted first to a conventional averaging circuit 155 which averages the incoming signals and the output of which transmits a signal denoting the average hardness of successive filter cigarettes or successive groups of filter cigarettes. The output of the averaging circuit 155 is connected with one input of a signal correcting circuit 161 which receives one or more additional signals serving to modify the signal which is transmitted by the output of the averaging circuit 155. The additional signals include signals from a device 162 which monitors the diameters of the filter cigarettes, from a device 163 which monitors the RPM of the conveyor 131, and (if necessary) from a device 164 which monitors the moisture content of the filter cigarettes. The reason for the provision of devices 162, 163 and 164 is that the parameters which are monitored by these devices can influence the signals from the averaging circuit 155, i.e., those signals which are indicative of monitored hardness of the filter cigarettes.

The diameter monitoring device 162 can include optical means for ascertaining the diameters of filter cigarettes 187. A suitable monitoring device is disclosed in U.S. Pat. No. 4,011,950 granted Mar. 15, 1977 to McLoughlin et al. for "Cigarette monitoring apparatus". If desired or necessary, the diameters of filter cigarettes can be ascertained while the filter cigarettes are transported by a discrete conveyor which precedes or follows the conveyor 131.

The device 163 which monitors the RPM of the conveyor 131 can include or constitute a conventional digital or analog tachometer.

The device 164 which serves to ascertain the moisture content of filter cigarettes 187 can comprise a capacitor 166 which is designed to determine the mass of the adjacent ends of filter cigarettes 187. Reference may be had to commonly owned U.S. Pat. No. 3,951,267 granted Apr. 20, 1976 to Reuland for "Apparatus for testing the end portions of cigarettes or the like". A circuit of the type disclosed in commonly owned U.S. Pat. No. 3,979,581 granted Sept. 7, 1976 to Reuland for "Method and arrangement for determining the mass of tobacco or the like by capacitance and attenuation measurements in a resonant high frequency oscillator circuit" can be used to process signals from the capacitor 167 so as to transmit signals which are indicative of the moisture content of tested filter cigarettes.

Signals which are transmitted by the circuit 155 are indicative of average hardness of the respective filter cigarettes because each such cigarette is tested at a plurality of spaced-apart locations (as seen in the longitudinal direction of the filter cigarettes). Such signals are then corrected or modified by signals from the devices 162, 163, 164 prior to being transmitted to the averaging circuit 144 and thence to the signal comparing stage 146 and (if so decided by the designer of the filter tipping machine FA of FIG. 3) to the circuit 98 of FIG. 2. The averaging circuit 144 averages the hardness of a relatively large number of successively tested filter cigarettes (such number can exceed 100) so as to ensure that an accidental departure from acceptable hardness will not initiate an adjustment of the rod making machine of FIG. 2 and/or of the tipping machine FA.

In order to ensure that the presence of gaps in the row of filter cigarettes on the conveyor 131 will not initiate adjustments of the rod making and/or tipping machine, the apparatus 142 of FIG. 4 further comprises means for preventing signals whose generation is initiated during advancement of gaps (absent filter cigarettes) through the testing region W from influencing the signals which are transmitted to the comparing stage 144 and to the signal correcting circuit 98 of FIG. 2. Such means constitutes a detector which generates signals in response to detection of empty flutes at the periphery of the conveyor 131. It is presently preferred to employ a photoelectric detector 167 which can constitute a reflection type photocell and transmits signals to the circuit 144. Such signals block the transmission of signals from the circuit 161 to the circuit 144, i.e., the circuit 144 cannot receive those signals which are generated by the detectors 158a–158d during travel of empty flutes through the testing region W.

FIG. 4 further shows that the extent of deformation (as at 168.1) of a filter cigarette 187.1 which has just entered the testing region W is relatively small; that such deformation (shown at 186.2 and 186.3) becomes more pronounced as a filter cigarette advances along the levers 151a–151d toward the discharge end of the testing region W; and that the deformation (shown at 168.4) gradually decreases while a filter cigarette continues to advance toward the discharge end of the region W. Such mode of deforming filter cigarettes 187.1 to 187.4 in the testing region W has been found to be especially suitable because it ensures gentle treatment of tested rod-shaped products.

The illustrated levers 151a–151d can be replaced with levers which are biased against the rod-shaped products in the testing region W by mechanical springs, by a compressed gaseous fluid or in any other suitable way. Furthermore, such levers can be replaced with force applicators which cause elastic deformation of rod-shaped products as a result of impingement of one or more currents or jets of compressed gaseous fluid so that the depressions 168.1–168.4 are formed by a gas rather than by the weight of a lever or the like.

It is further within the purview of the invention to employ an apparatus which generates pneumatic signals in lieu of electric signals. For example, if the levers 151a–151d are replaced with nozzles which blow jets or currents of a compressed gaseous medium to elastically deform selected portions of cigarettes in the testing region W, the apparatus can employ pneumatic detectors which transmit pneumatic signals denoting the extent of elastic deformation of the rod-shaped products, and such pneumatic signals are then processed in a manner analogous to the described in connection with FIG. 4.

It is further possible to replace the measuring devices 68 and 69 of FIG. 2 with a strain gauge which determines the extent of compression of the trimmed stream 74 during draping into the web 76 in the wrapping mechanism 79. However, it is presently preferred to employ the aforedescribed parts 66, 68, 69 and 84 which are not capable of directly ascertaining the hardness or filling power of the stream or filler but are designed to transmit signals denoting other characteristics and capable of being processed into signals which are indicative of hardness. As explained in connection with FIG. 2, devices which are used for indirect determination of hardness of rod-shaped products 87 can serve to monitor the height of the stream, the mass flow of fibrous material, the resistance of the stream to penetration by a gaseous fluid and/or the resistance which the stream or the filler (i.e., a converted stream) offers to penetration by corpuscular radiation. The manner of processing such indirect signals into signals denoting the hardness of rod-shaped products is fully disclosed in the aforementioned commonly owned Reuland U.S. Pat. No. 4,280,516. Indirect determination of hardness of rod-shaped products 87 prior to actual subdivision of the rod 83 into such products is desirable and advantageous because this renders it possible to immediately obtain information denoting whether the hardness is or is not acceptable and to undertake corrective measures without any delay so that the number of rejects is reduced accordingly. Moreover, long-range departures from optimum hardness of the products 87 are effectively prevented by employing the signal correcting circuit 98 which receives signals from the improved hardness measuring apparatus, i.e., from an apparatus which can determine the hardness of rod-shaped products 87 with a degree of reliability normally greatly exceeding that of the function generator 91 and the associated detectors 84, 96.

The feature of using two hardness monitoring apparatus in or with a filter tipping machine in a manner as described in connection with FIG. 3 or in a similar manner is believed to be novel and patentable irrespective of the nature of apparatus which are used to ascertain the hardness of plain cigarettes 87 and of the filter cigarettes 187. Thus, at least one of the apparatus 141, 142 can be replaced with any conventional apparatus (which is capable of ascertaining the hardness of elastically deformable rod-shaped products) without departing from the spirit of the invention. However, it is presently preferred to combine the filter tipping machine FA with at least one apparatus of the type shown in FIG. 4 because such apparatus can ascertain the hardness of rod-shaped products in a highly reliable manner and without affecting the appearance and/or other desirable characteristics of the tested products.

If desired, the apparatus 141 can be placed immediately downstream of the cutoff 86 of FIG. 2 and/or the apparatus 142 can be placed downstream of the belt conveyor 136. In other words, these apparatus need not be installed directly in or on the tipping machine FA as long as they can be used to ascertain the differences in hardness which are caused by the constituents of the filter tipping machine.

An advantage of the feature that signals at the output of the function generator 91 and at the outputs of the signal correcting circuits 98, 97 can influence the setting of the valve 50, and hence the pressure in the suction chamber 48, is that this renders it possible to rapidly influence the hardness of rod-shaped products 87 without altering the distance Ht, i.e., without changing the level of the trimming discs 62 relative to the lower reach of the conveyor 44 and/or vice versa. As a rule, it is preferred to avoid frequent changes in the level of the trimming device and/or in the level of the conveyor which transports a surplus carrying stream of fibrous material past the trimming device.

An important advantage of the improved apparatus is its versatility. Thus, the apparatus can take into consideration any desired number of parameters which are likely to influence the accuracy of determination of hardness of rod-shaped products of the tobacco processing industry. Such signals can be used to influence the making of the cigarette rod 83 so as to ensure that the hardness of each plain cigarette 87 will match or closely approximate an optimum value and/or to enable the persons in charge of the filter tipping machine FA to ascertain the changes of hardness which take place during conversion of plain cigarettes 87 and filter plugs into filter cigarettes 187. Moreover, the apparatus can treat the rod-shaped products gently because the deformation of such products remains within the elastic limits. Still further, the testing operation is reliable because each and every cigarette is tested at several spaced-apart locations and during travel through a relatively long testing zone (region W).

While it is possible to employ a single mechanical or pneumatic force applicator (e.g., only one of the levers 151a–151d), it is presently preferred to operate with two or more force applicators in order to enhance the reliability of the hardness measuring operation. Thus, and as described with reference to FIG. 4, signals denoting the deformation of a filter cigarette 187 at a plurality of spaced-apart locations can be averaged (as at 155) in order to generate a signal which is more accurately representative of average hardness of the tested product.

It is further clear that the improved apparatus can be modified in such a way that a single lever or two or more levers can deform only one rod-shaped product at a time. The illustrated design, wherein several levers simultaneously apply forces to several successive rod-shaped products, is preferred at this time because it has been found that such mode of testing contributes to more uniform testing and to actual smoothing of tested portions of the products. Moreover, the operation is more reliable because the levers 151a–151d need not pivot through large angles but merely dwell in certain angular positions of oscillate only negligibly as a result of engagement with successive cigarettes of the row of cigarettes on the conveyor of the transporting unit of the respective apparatus.

The feature that the extent of elastic deformation of a rod-shaped product gradually increases as the product advances from the receiving end toward the discharging end of the testing region W also contributes to more satisfactory determination of hardness of the products as well as to gentler treatment of the products. Thus, if an oncoming product were abruptly subjected to maximum elastic deformation (such as shown at 186.2 and 186.3 in FIG. 4), the wrapper of such product would be likely to be defaced, or even damaged, e.g., by bursting of the seam of the respective plain cigarette. Gradual elastic deformation of products which advance through the testing region W effectively eliminates or at least greatly reduces the danger of damage to the wrappers of tested products.

Gradual reduction of deforming force as the products approach the discharge end of the testing region W also contributes to effectiveness of the improved apparatus. Thus, if the levers 151a–151d perform any angular movements at all, the extent of such angular movements will not undergo an abrupt change when a freshly tested product leaves the testing region W.

The provision of the diameter measuring or monitoring device 162 is desirable and advantageous when the force applying means comprises mechanical force applicators (such as the levers 151a–151d) because the extent of elastic deformation of rod-shaped products by levers or like members which rest on the advancing products by gravity is a function of the diameters of the products.

The detector 167 of gaps in the series of rod-shaped products on the transporting unit of the improved apparatus also constitutes an optional but highly desirable and advantageous component of the improved apparatus. Such detector ensures that signals which are generated by the detectors 158a–158b during travel of an empty flute past the levers 151a–151d cannot distort the averaged signals from the circuit 155 and hence the signals which are transmitted from the circuit 143 or 144. As mentioned above, the detector 167 simply prevents the circuit 143 or 144 from accepting signals which are generated by the detectors 158a–158d during travel of an empty flute past the levers 151a–151d. Alternatively, or in addition to the detector 167, signals which are generated by the detectors 158a–158d during travel of an empty flute through the testing region W can be eliminated from consideration by the simple expedient of monitoring the train of signals to or from the circuit 143, 144 and suppressing those signals which are clearly indicative of the absence of a rod-shaped product at the testing station (i.e., those signals which are indicative of products having a hardness well below that of any products likely to reach the testing region W).

The conveyor 89 at the inlet end AB of the filter tipping machine FA can be installed at another locus, e.g., in the region of the assembly conveyor 103. However, the illustrated location of the apparatus 141 is preferred at this time because this ensures that signals denoting the hardness of plain cigarettes 87 can be generated close to the rod making machine, i.e., that such signals are available practically instantaneously following subdivision of the rod 83 into discrete plain cigarettes 87. This ensures that signals which the circuit 98 receives from the function generator 91 can be corrected (if and when necessary) with a minimum of delay, especially if the rod making machine of FIG. 2 is directly coupled to the filter tipping machine FA of FIG. 3.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of ascertaining the hardness of cigarettes and analogous rod-shaped smokers' products which are capable of undergoing elastic deformation, comprising the steps of transporting the products substantially transversely of their axes along at least one predetermined path; applying to the products a predetermined force in the course of the transporting step so as to subject the products to elastic deformation; monitoring the extent of elastic deformation of the products; and generating signals denoting the extent of elastic deformation of the products.

2. The method of claim 1, wherein said signals are electric signals.

3. The method of claim 1, further comprising the steps of applying to the products at least one additional force so as to subject the products to additional elastic deformation, monitoring the extent of additional elastic deformation of the products, generating additional signals denoting the extent of additional elastic deformation of the products, and converting the first named signals and the additional signals into further signals denoting the average elastic deformation of the products.

4. The method of claim 3, wherein said signals are electric signals.

5. The method of claim 3, wherein said force of predetermined magnitude is applied to first portions of the products and said additional force is applied to different additional portions of the products.

6. The method of claim 1, wherein said transporting step includes conveying the products on an endless conveyor.

7. The method of claim 6, wherein the conveyor is a rotary drum having axially parallel peripheral flutes for the products.

8. The method of claim 1, wherein said transporting step includes conveying the products in the form of a series of successive products, said force applying step including simultaneously applying force to at least two successive products of said series.

9. The method of claim 8, wherein said force applying step includes applying to the products a mechanical force.

10. The method of claim 8, wherein said transporting step takes place in a filter tipping machine.

11. The method of claim 8, wherein said force applying step includes the application of a first force in a first portion and the application of a second force in a second portion of said at least one path.

12. The method of claim 8, wherein said force applying step includes gradually increasing the magnitude of force in a predetermined portion of said at least one path.

13. The method of claim 12, wherein said force applying step further comprises gradually decreasing the magnitude of the force in a second portion of said path downstream of said predetermined portion.

14. The method of claim 1, wherein said force applying to the products step includes applying the weight of a mechanical deforming member.

15. The method of claim 14, wherein said weight is a substantially constant weight.

16. The method of claim 1, further comprising the steps of monitoring the diameters of the products, generating additional signals denoting the monitored diameters of the products, and modifying the signals denoting the extent of elastic deformation of the products as a function of said additional signals.

17. The method of claim 1, wherein said transporting step includes conveying the products in the form of a row consisting of a series of parallel products and having gaps as a result of randomly occurring absence of products, said force applying step including applying the predetermined force at intervals corresponding to the frequency of conveying successive products and gaps along a predetermined portion of said path, said signal generating step including generating a signal during each of said intervals and further comprising the step of processing only those signals which are generated as a result of elastic deformation of products in said predetermined portion of said path.

18. The method of claim 1 of ascertaining the hardness of products wherein a rod-like elastically deformable stream of fibrous material is draped into a web of wrapping material and the wrapped stream is subdivided into rod-shaped products each of which contains a portion of the stream, further comprising the steps of monitoring at least one parameter of said portions of the stream, generating additional signals denoting the at least one parameter of said portions of the stream, and modifying said additional signals as a function of signals denoting the elastic deformation of corresponding products.

19. The method of claim 18, wherein said at least one parameter is the hardness of said portions of the stream.

20. The method of claim 18, wherein said at least one parameter is the filling power of fibrous material in said portions of the stream.

21. The method of claim 18, wherein said modifying step includes influencing said additional signals so as to maintain the hardness of the products within a predetermined range.

22. The method of claim 18, wherein said parameter monitoring step includes indirectly monitoring the at least one parameter of said of the stream.

23. The method of claim 18, wherein said parameter monitoring step includes indirectly monitoring the at least one parameter of said portions of the stream.

24. The method of claim 18, wherein said parameter monitoring step includes monitoring the height of the stream.

25. The method of claim 18, wherein said parameter monitoring step includes directing against the stream at least one beam of radiation and ascertaining the quantity of radiation which penetrates through the stream.

26. The method of claim 18, wherein said parameter monitoring step includes monitoring the mass flow of the material of the stream.

27. The method of claim 18, wherein said parameter monitoring step includes directing against the stream at least one current of a gaseous fluid and ascertaining the extent of penetration of gaseous fluid through the stream.

28. Apparatus for ascertaining the hardness of cigarettes and analogous rod-shaped smokers' products which are capable of undergoing elastic deformation, comprising means for transporting the products substantially transversely of their axis along at least one predetermined path; means for applying to the products which are being transported along said path a predetermined force so as to subject the products to elastic deformation; and means for monitoring the extent of elastic deformation of the products, including means for generating signals denoting the extent of elastic deformation of the products.

29. The apparatus of claim 28, wherein said force applying means includes at least one mechanical force applicator which acts upon the products in a predetermined portion of said path.

30. The apparatus of claim 28, wherein said force applying means includes a plural of mechanical force applicators which are adjacent each other and are operative to elastically deform different portions of transported products.

31. The apparatus of claim 30, wherein said monitoring means includes a discrete monitoring device for each of said force applicators, said signal generating means including means for generating discrete signals denoting elastic deformation of products by each of said mechanical force applicators, and further comprising means for converting said discrete signals into further signals denoting average elastic deformation of the products.

32. The apparatus of claim 28, wherein said transporting means comprises an endless conveyor.

33. The apparatus of claim 32, wherein said conveyor is a rotary drum.

34. The apparatus of claim 28, wherein said force applying means includes at least one mechanical force applicator which is arranged to simultaneously deform a plurality of products in said path.

35. The apparatus of claim 34, wherein said transporting means comprises a conveyor having means for advancing a series of successive parallel products along said at least one predetermined path, said applicator including means for subjecting successive products of said series to the action of a progressively increasing deforming force in a predetermined portion of said path.

36. The apparatus of claim 35, wherein said applicator further includes means for subjecting successive products of said series to the action of a progressively decreasing deforming force in a second portion of said path.

37. The apparatus of claim 36, wherein said second portion is located downstream of said predetermined portion.

38. The apparatus of claim 28, wherein said force applying means includes at least one lever and means for pivotally mounting said lever so that the lever rests on the products in a predetermined portion of said path.

39. The apparatus of claim 28, further comprising means for monitoring the diameters of the products including means for generating additional signals denoting the diameters of the products, and means for modifying the signals denoting the extent of elastic deformation of the products as a function of the corresponding additional signals.

40. The apparatus of claim 28, wherein said transporting means includes means for conveying the products in the form of a row consisting of a series of parallel products and having gaps as a result of randomly occurring absence of products, said force applying means including means for applying the predetermined force at intervals corresponding to the frequency of conveying successive products and gaps along a predetermined portion of said path so that said signal generating means generates a first signal during each of said intervals, and further comprising means for monitoring said path for the presence of said gaps including means for generating second signals denoting the presence of gaps, means for processing first signals denoting the extent of deformation of products in said portion of said path, and means for preventing transmission to said processing means of those first signals which are generated during intervals when said gaps are conveyed along said portion of said path.

41. Apparatus for ascertaining the hardness of cigarettes and analogous rod-shaped products which a re capable of undergoing elastic deformation and wherein a stream of fibrous material is advanced along at least one predetermined path, comprising means for transporting the products substantially transversely of their axes along a first portion of said at least one path; means for applying to the products which are being transported along said at least one path a predetermined force so as to subject the products to elastic deformation; means for monitoring the extent of elastic deformation of the products, including means for generating first signals denoting the extent of elastic deformation of the products; means for supplying fibrous material into a second portion of said at least one path upstream of said first portion so that the material is entrained by and forms a stream on said transporting means; means for draping the stream into a web of wrapping material in a third portion of said at least one path downstream of said second portion and upstream of said first portion so as to convert the stream and the wrapping material into a succession of said rod-shaped products; means for monitoring the hardness of the stream, including means for generating second signals denoting the monitored hardness of the stream; and means for modifying said second signals as a function of said first signals.

42. Apparatus for ascertaining the hardness of cigarettes and analogous rod-shaped products which are capable of undergoing elastic deformation and wherein a stream of fibrous material is advanced along at least one predetermined path, comprising means for transporting the products substantially transversely of their axes along a first portion of said at least one path; means for applying to the products which are being transported along said at least one path a predetermined force so as to subject the products to elastic deformation; means for monitoring the extent of elastic deformation of the products, including means for generating first signals denoting the extent of elastic deformation of the products; means for supplying fibrous material into a second portion of said at least one path upstream of said first portion so that the material is entrained by and forms a stream on said transporting means; means for draping the stream into a web of wrapping material in a third portion of said at least one path downstream of said second portion and upstream of said third portion so as to convert the stream and the wrapping material into a succession of rod-shaped products; means for monitoring the filling power of the fibrous material of the stream, including means for generating second signals denoting the monitored filled power of the fibrous material of the stream; and means for modifying said second signals as a function of said first signals.

* * * * *